United States Patent [19]

Linde

[11] Patent Number: 5,792,452
[45] Date of Patent: Aug. 11, 1998

[54] LIVE SALMONELLA VACCINE HAVING AN INCREASED STABILITY

[76] Inventor: Klaus Linde, Bornaische Strasse 137, D-04279 Leipzig, Germany

[21] Appl. No.: 317,195

[22] Filed: Oct. 3, 1994

[30] Foreign Application Priority Data

Oct. 4, 1993 [DE] Germany .......................... 43 33 742.2

[51] Int. Cl.$^6$ .......................... A61K 45/00; A61K 45/05; A01N 63/00; C12N 1/36
[52] U.S. Cl. .................. 424/93.4; 424/278.1; 424/282.1; 424/821; 424/826; 424/258.1; 435/245; 435/252.2
[58] Field of Search .............................. 424/282.1, 278.1, 424/821, 826, 258.1, 93.4; 435/245, 252.1

[56] References Cited

U.S. PATENT DOCUMENTS

| 4,472,378 | 9/1984 | Shuster et al. | 424/92 |
| 4,687,737 | 8/1987 | Sharp et al. | 435/68 |

FOREIGN PATENT DOCUMENTS 218834  2/1985  Germany .

OTHER PUBLICATIONS

Linde, K. Arch. Exper. Vet. Med. Salmonella mutants with shortened generation times. vol. 36, pp. 237–242, Feb. 2, 1982.

Linde et al., "Prophylaxis of *Salmonella abortus* ovis-induced abortion of sheep . . . " 1992, pp. 337–340.

Linde et al. "Stabe *Listeria monocytogenes* live vaccine candidate strains . . . ", 1991, pp. 101–105.

*Primary Examiner*—David M. Naff
*Assistant Examiner*—Deborah K. Ware
*Attorney, Agent, or Firm*—Thomas M. Scofield

[57] ABSTRACT

A live Salmonella vaccine having an increased stability is disclosed. Further, immunization methods of a host such as chickens against Salmonella diseases are carried out by the use of the vaccine. The vaccine may be administered orally or parenterally and includes one or more of the live vaccines disclosed herein. The live vaccine is produced from one or more live vaccine strains with metabolic drift attenuation via an increased generation time. The vaccine is an immunogenic, stable and single or multiple marker live vaccine strain with or without envelope mutation; and the live vaccine is a suppressor mutant of an original live vaccine strain still having the attenuation marker(s) of the original live vaccine strain but a shortened generation time and having macrolide tolerance.

3 Claims, No Drawings

LIVE SALMONELLA VACCINE HAVING AN INCREASED STABILITY

The invention relates to a live vaccine having an increased stability. In comparison to the known live vaccines the stability is increased by at least the factor $10^{-7}$. The vaccine consists of at least one metabolic drift attenuated, immunogenic live vaccine strain with or without envelope mutation and an attenuation level optimally adapted to the host species. Possible host species are working animals and humans. One embodiment proposes a live vaccine for chicks and chickens for the immunization against Salmonella.

The features of the vaccine strain and its production will be described.

The safety of bacterial live vaccine strains is internationally guaranteed by deletions, the stability of which lying in the range of about $10^{-12}$ (calculated from the in vivo repair of single marker Shigella over genetically related coli, proven by tests on volunteers (Formal et al., as well as DuPont et al.: Immunbiol. Standard; Karger; Basel/Munich/ New York 1971, 15, 73–78 as well as 213–218). With the known double marker (spot mutation) attenuation, in the most disadvantageous case, a total stability (as a product of individual stabilities) of at least $10^{-14}$ results. According to the object of the present invention, this total stability is to be increased to at least $10^{-21}$, wherein the stability of (as a rule not usual) two (set at separate gene locations) attenuated deletions is achieved.

The high requirements of the World Health Organisation and the wide-spread opinion about the alleged instabilities in the use of live vaccines under practical conditions let it appear to be necessary to enhance the already existing safety buffer having a stability of $10^{-14}$ by yet another increase of the attenuation to at least the factor $10^{-21}$, and to raise the stability of the antiepidemic potency provided by an envelope marker to at least $10^{-14}$. In the construction of such live vaccines having an increased stability well-established and known principles are to be used and elaborated.

It is known that a special difficulty in the search for effective and well-tolerated vaccine strains lies in the question whether the marker-conditioned attenuation level ("metabolic defect") and the sensitivity characteristic of a host species for the possible pathogene are correlated such that

- still a limited but sufficient in vivo propagation of the vaccine strain is possible, and therefore an immunity relevant in practice results,
- in the case of a too low sensitivity and simultaneously relatively severe "metabolic disturbance" of the vaccine strain a more or less distinct overattenuation occurs, and therefore (not relevant in practice) several vaccinations are necessary, as e. g. in the case of S.typhi gal-E 21a,
- in the case of high sensitivity and simultaneously relatively minor "metabolic disturbances" of the vaccine strain the "remaining virulence" triggers unacceptable side effects.

As an almost classical example of the correlation between marker-conditioned attenuation level, sensitivity of the host species, and immunogenicity the effectiveness of the vaccine Zoosalora—Salmonella tyhimurium His⁻(attenuation by co-mutation)Pur⁻, i. p. $LD_{50}$ mouse $10^{8.2}$ (wild strain about $10^1$) cfu—in mice, calves and chickens: referring to one kg body weight the parenteral $LD_{50}$ (as a degree of sensitivity) in mice is about $10^3$, in calves about $5\times10^6$ and in chicks/chickens about $5\times10^8$ germs. Therefore, in the case of a single oral immunization Zoosaloral protects mice with >95% against a lethal challenge, calves still with a relevance in practice (in the case of an $LD_{75}$ challenge "only" 36% of the immunized animals die), in chicks/chickens, however, it fails because of overattenuation (Linde, K. et al.: Vaccine, 1990, 8, 278–282).

This means that the characteristic sensitivity level of the host species to the respective pathogen has to be compensated by a corresponding attenuation level to achieve a resilient immunity with a single immunization. This, in itself logical (but apparently not observed and not formulated, respectively) rule can be met for the first time with relevance in practice by revealing the principle "attenuation by means of metabolic drift mutations" in essential enzymes and metabolic compartments as e. g. RNA polymerase, gyrase, ribosome proteins (isolation by means of chromosomal, e. g. rifampicin, streptomycin, nalidixic acid resistance). Since in this principle the logarithm of the $LD_{50}$ (measured in the sensitive test animal) correlates linearly with the (prolonged) generation time, also the (prolonged) generation time can serve as an attenuation equivalent for pathogens where a suitable (sensitive) test animal is missing. The principle "attenuation by means of metabolic drift mutations" is described comprehensively in DD 155294, DD 218834, DD 235828, DD 253182, DD 253184, DD 281118, DD 294420, EP 0263528, as well as in the publications:

Linde, K.: Zbl. Bakt. Hyg. I. Abt. 1981, 249, 350–361

Linde, K.: Dev. Biol. Standard 1983, 53, 15–28

Linde, K.: Arch. exper. Vet. med. 1982, 36, 647–656

Linde, K. et al.: Arch. exper. Vet. med. 1983, 37, 353–360

Linde, K. et al.: Vaccine 1990, 8, 25–29

Linde, K. et al.: Vaccine 1990, 8, 278–282

Linde, K. et al.: Vaccine 1991, 9, 101–1105

Linde, K. et al.: Vaccine 1992, 10, 337–340

Linde, K. et al.: Vaccine 1993, 11, 197–200

Marakusha, B. I. et al.: Z. Microbiol. Epidemiol. Immunol. 1987/4, 3–8.

These vaccine strains in which one of the attenuating metabolic drift markers is usually a chromosomal nalidixic acid resistance (gyrase) mutation can be optimized by means of hst (high sensitivity to tensides and macrolide antibiotics), rbt (reversion to bile tolerance) or rtt (reversion to tenside tolerance) markers. These markers reduce the excretion and the capability of survival of the vaccine strains in the environment without a significant influence on the parenteral virulence behaviour.

The antiepidemic markers are described comprehensively in DD 218836, DD 231491, DD 253182, DD 253183, DD 252184, and EP 0263528, as well as in the publications:

Linde, K.: Arch. exper. Vet. med. 1982, 36, 657–662

Linde, K.: Dev. Biol. Standard 1983, 53, 15–28

Linde, K. et al.: Vaccine 1990, 8, 278–282.

Finally, an envelope marker was suggested which combines the features of the antiepidemic markers with those of a safety-/and therapy marker. The prototype of such an envelope marker is the so-called Ssq (supersensitivity to (fluor-) quinolones)-marker which, in the Sm/Rif metabolic drift combination, next to the antiepidemic potency, a. o. provides a supersensitivity to the antibiotic ciprofloxacin, presently the most effective against salmonella.

The common feature of vaccine strains produced by using two separately attenuated metabolic drift markers as well as a combination of metabolic drift and envelope and antiepidemic markers, respectively, is that their reversion frequency with respect to the attenuated markers is usually restricted to a factor of $\leq 10^{-14}$, and with respect to the envelope marker-conditioned antiepidemic potency of selected clones to a factor of $\leq 10^{-8}$, which is generally sufficient under practical conditions.

Therefore, it is the object of the invention to increase the stability of the vaccine serving for the production of the vaccine strain(s) such that, with respect to the attenuation, a stability of at least $10^{-21}$ and, with respect to the antiepidemic potency, of at least $10^{-14}$ is achieved. Here, known advantageous principles for the adaptation of the attenuation depending on the sensitivity of the host species and the influence on the excretion and capability of survival of the vaccine strains in the environment are to be kept and improved further.

This object is attained by providing a live vaccine, a special live vaccine for chickens and chicks, a method for the production of such live vaccines, and live vaccine strains as well as their use.

In one embodiment, a live vaccine produced from at least one metabolic drift attenuated, immunogenic, stable single or multiple marker vaccine strain with or without envelope mutation and an optimal attenuation level adapted to the sensitivity of the host species is used. According to the invention, as vaccine strain its revertant, as a suppressor mutant still having the attenuation or/and the envelope marker, is used.

In a preferred embodiment, as vaccine strains its revertant having a shortenend generation time is used, wherein this revertant, as a suppressor mutant, has one or more attenuating metabolic drift markers. The revertant has a similar as or an only slightly lower attenuation level than the original vaccine strain.

In a further preferred embodiment, as vaccine strain its macrolide tolerant revertant is used, wherein this revertant, as a suppressor mutant, still has the envelope marker. The revertant has a similar as or an only slightly higher antiepidemic potency than the original vaccine strain.

In a third preferred embodiment, as vaccine strain its double revertant is used, wherein this revertant having a shortened generation time and a macrolide tolerance, as a suppressor mutant, has one or more attenuating metabolic drift markers and also still has the envelope marker.

Surprisingly, it has been found that, starting from metabolic drift attenuated vaccine strains with or without additional envelope marker, the revertants having a shortened generation time or/and a macrolide tolerance possess an unchanged attenuation and antiepidemic potency, which proves that the metabolic drift attenuation or/and envelope marker of the original vaccine strains still exist in the revertant. Furthermore, it has been shown that during the transition from the original vaccine strains to their revertants/suppressor mutants the attenuation in the sense of an adaptation to the sensitivity of the host species can still be varied to a small extent. The same stands for the antiepidemic potency.

As an example for the live vaccine the following Salmonella vaccine strains for a live vaccine for the oral immunization of chicks as well as the oral or parenteral immunization/boostering of chickens against Salmonella infections are proposed, which have been derived from original vaccine strains having a generation time of about 31 to 32 minutes and/or an MIC of erythromycin of $\leq 5$ µg/ml. The revertants having a shortened generation time:

S.*tm* Ssq/Sm 60/Rif 42/-GVR II 30 generation time about 26.0 minutes

S.*ent* Ssq/Sm 24/Rif 12/-GVR II 30 generation time about 27.0 minutes

S.*inf* Ssq/Sm 153/Rif 7/-GVR II 30 generation time about 25.0 minutes

S.*ana* Ssq/Sm 81/Rif 21/-GVR II 30 generation time about 26.5 minutes show a generation time of $\leq 27$ minutes. In the case of revertants having a macrolide tolerance:

S. *tm* Ssq-MTR 16/Sm 60/Rif 42

S. *ent* Ssq-MTR 25/Sm 24/Rif 12

S. *inf* Ssq-MTR 12/Sm 153/Rif 7

S. *ana* Ssq-MTR 23/Sm 81/Rif 21 the MIC of erythromycin was increased from $\leq 5$ µg/ml to $\geq 20$ µg/ml.

The listed revertants/suppressor mutants have been derived from the following Salmonella vaccine strains, deposited at the DSM—Deutsche Sammlung von Mikroorganismen und Zellkulturen GmbH, D-38124 Braunschweig, Germany:

| S. *tm* Ssq/Sm 60/Rif 42 | DSM 8433 |
| S. *ent* Ssq/Sm 24/Rif 12 | DSM 8435 |
| S. *inf* Ssq/Sm 153/Rif 7 | DSM 8434 |
| S. *ana* Ssq/Sm 81/Rif 21 | DSM 8441. |

The revertants/suppressor mutants according to the invention represent a new generation of increasingly stable (total stability=product of the markers of the original vaccine strains and the suppressor mutants) vaccine strains. They use the surprisingly found rule that reversions/suppressor mutations to the pseudo wild type with unchanged or only slightly lower attenuation level and/or unchanged or only slightly varying antiepidemic potency occur significantly more often than back mutations. It was tested in how far this can also be used for testing the actual stability of the metabolic drift attenuation and envelope markers, and, at the same time, for gaining a new generation of extremely stable vaccine strains which comply ideally with the stability-/and safety requirements postulated by the WHO (Report of the WHO Scientific Group: Oral Enteric Bacterial Vaccines, World Health Organisation, Technical Report Series No. 500, 1972), and which, in view of these now triple marker attenuated vaccine strains, reduces the discussion about the stability of double marker vaccine strains impeding the vaccine introduction to absurdity. The safety of bacterial live vaccine strains is internationally guaranteed by deletions (see above), the stability of which lying in the range of about $10^{-12}$ (calculated from the in vivo repair of single marker Shigella over genetically related *coli*), proven by tests on volunteers (Formal et al., as well as DuPont et al.: Immunbiol. Standard; Karger; Basel/Munich/New York 1971, 15, 73–78 as well as 213–218). With the known double marker (spot mutation) attenuation, in the most disadvantageous case, a total stability (as a product of individual stabilities) of at least $10^{-14}$ results. An additional suppressor mutation therefore increases the total stability to at least $10^{-21}$, and thus the stability of (as a rule not usual) two (set at separate gene locations) attenuating deletions is achieved. Upon coupling two attenuating metabolic drift markers with an envelope mutation and subsequent production of the suppressor mutation of both principles a total stability of $\leq 10^{-35}$ would even result, which is not necessary as such—since according to the WHO's definition a mutation interrupting the infection chains of a vaccine strain is to be seen as an attenuation marker (WHO Technical Report Series No. 500, 1972).

Depending on the markers, two kinds of revertants are differentiated between and will be described in the following.

REVERTANTS HAVING A SHORTENED GENERATION TIME (GVR)

The stability of the metabolic drift (antibiotic resistance mutation) attenuation together with a corresponding (increased in Salmonella vaccine strains for chicks/chickens from 22 to 31–32 minutes) prolongation of the generation time can only be proven indirectly by the received resistance and the defined prolonged generation time.

Slowly growing metabolic drift attenuated vaccine strains, however, offer a selective advantage for clones where further mutations (because there is no genetic stability as such) lead to shorter generation times by means of "corrected" metabolic sequences. This means, that an enrichment of GVR strains can be reckoned with under the corresponding selection pressures in a vaccine strain population growing more slowly.

The conclusion based on the known prior art that "prolongation of generation time leads to attenuation" and therefore "shortening of generation time (inversely proportional) leads to increased virulence" is now proven wrong in the knowledge about the importance of reversions/suppressor mutants (which occur significantly more often than back mutations) (Linde, K.: Arch. exper. Vet. med. 1978, 32, 943).

In the following example 1 by means of the well-established model S.typhimurium/mouse direct proof will be offered for the fact that the GVR's attenuation (in relation to the original vaccine strain) is unchanged or only slightly lower and, therefore, they still have their original attenuation markers. These revertants/suppressor mutants having a shortened generation time therefore represent a new type of extremely stable vaccine strains, the reversion frequency of which being at maximum $\leq 10^{-21}$ (total stability=product of the individual stabilities (when assuming an unlikely high scale of $\leq 10^{-7}$ per single marker): Sm×Rif×suppressor mutation).

MACROLIDE TOLERANT REVERTANTS (MTR)

The reversion frequency of the envelope mutation taken from the number of 20 µg erythromycin tolerant clones in general lies between $10^{-6}$ and $10^{-8}$ and only in the case of a few selected strains is $\leq 10^{-8}$.

It has been found that the macrolide tolerant clones—despite a regained wild strain tolerance to erythromycin as well as generally the loss of the supersensitivity to ciprofloxacin, doxycycline, chloramphenicol—in their antiepidemic function (reduced capability of survival in the environment and shortened excretion in chicks) approximately correspond to the original strain or only vary slightly around its values and therefore still have the original envelope mutation.

Details can be taken from the following example 2.

These macrolide tolerant revertants/suppressor mutants therefore represent a new type of extremely stable vaccine strains, the reversion frequency of which being at maximum $10^{-14}$ in the antiepidemic potency (total stability=product of the original envelope marker and the suppressor mutation).

Therefore, the revertants having shortened generation times and/or a macrolide tolerance which have been derived from metabolic drift attenuated single or multiple marker original vaccine strains with or without additional antiepidemic envelope marker lead to vaccine strains which, to a great extent, comply with the strict requirements for the use of live vaccines under practical conditions.

The object of producing a live vaccine having an increased stability is attained by using at least one metabolic drift attenuated, immunogenic, stable single or multiple marker live vaccine strain with or without envelope mutation and an attenuation level optimally adapted to the host species. According to the invention, starting from a metabolic drift attenuated original vaccine strain without or with additional envelope mutation and an attenuation adapted to the host species and, at the same time, a defined prolonged generation time, the revertant having a shortened generation time and a macrolide tolerance is isolated. This suppressor mutant, still having the attenuation or/and envelope marker of the original vaccine strain, is used as increasingly stable vaccine strain, from which the live vaccine is produced by means of methods known as such.

In further embodiments of the method according to the invention, the conditioning features in comparison to the original vaccine strain can possibly still be influenced by means of the suppressor mutant.

In the case of strain dependent preferred separation of a revertant having a shortened generation time with a slightly lower attenuation level, an original vaccine strain with a higher (possibly up to the limit of overattenuation) attenuation is used for the isolation of an optimally attenuated supressor mutant.

For the production of a vaccine having an increased stability in the antipidemic potency, a revertant having a similar as or a slightly higher antiepidemic potency than the original vaccine strain is used.

By using this method in an arbitrary order, from a metabolic drift attenuated original vaccine strain having a macrolide sensitivity (envelope) marker, a revertant having a shortened generation time as well as a macrolide tolerance is obtained.

As an example for the method described above, one of the following methods for the production of a vaccine optimally adapted to chicks or chickens is proposed according to the invention.

For the production of the vaccine an increasingly stable vaccine strain is selected, the original vaccine strain of which having a generation time prolonged from about 22 minutes to about 31 to 32 minutes in comparison to the wild strain which, in the case of the revertant having a shortened generation time, is shortened to up to $\leq 27$ minutes.

A further method is characterized by the selection of a vaccine strain having an increased stability in the antiepidemic potency, the original vaccine strain of which having a macrolide sensitivity which, in the case of the macrolide tolerant revertant, results in an increase of the MIC of erythromycin from $\leq 5$ µg/ml to $\geq 20$ µg/ml.

Finally, both methods can also be combined in an arbitrary order by selecting a revertant having a shortened generation time as well as a macrolide tolerance from a metabolic drift attenuated original vaccine strain with macrolide sensitivity (envelope) marker for the production of a live vaccine having an increased stability. As vaccine strain one or more of the vaccine strains are used.

In the following examples the live vaccine and the method for the production of the live vaccine are to be described in detail.

MATERIAL AND METHOD

Strains Used wild strains

*Salmonella (S.) typhimurium, S.enteritidis, S.infantis, S.anatum* sets of metabolic drift double (triple) marker (total stability as a product of the individual stabilities) vaccine strains with an additional envelope marker and a graded attenuation/graded prolonged generation time (GT) (as attenuation equivalent) as well as further deposited vaccine strains as e. g.

S.*typhimurium* Ssq/Sm 60/Rif 42 GT:≈31 min. deposit no. DSM 8433

S.*enteritidis* Ssq/Sm 24/Rif 12 GT:≈32 min. deposit no. DSM 8435

S.*infantis* Ssq/Sm 153/Rif 7 GT:≈31 min. deposit no. DSM 8434

S.*anatum* Ssq/Sm 81/Rif 21 GT:≈32 min. deposit no. DSM 8441

S.*typhimurium* Nal 2/Rif 9/Rtt GT:≈32 min.

(location of deposit: DSM—Deutsche Sammlung von Mikroorganismen und Zellkulturen GmbH Braunschweig)

Used test and working animals for testing the respective mutants of the sets by means of methods known as such chicken chicks (laying brown eggs, vaccinated against Marek)

ICR and Prob 01 mice.

EXAMPLE 1

Revertants Having a Shortened Generation Time (GVR), derived from metabolic drift attenuated Salmonella original vaccine strains (with envelope marker) for chicks/chickens, as vaccine strains having an increased stability in the attenuation.

The original vaccine strains (with envelope marker) are vaccinated in 50 ml of nutrient bouillon (or in any other liquid medium), and are then passaged continuously with the dilution factor≦1:1000.

Marker Controls:

After each time four passages the received growth on nutrient agar with (12.5 μg nalidixic acid/ml or) 200 μg streptomycin/ml as well as 200 μg rifampicin/ml (as well as the missing growth with 20 μg erythromycin) is tested by means of a vaccine swab.

Within the 30 passages controlled the markers were stable.

Determination of Generation Time (GT) in the MS-2 Test System (Abbott):

In liquid cultures (nutrient, LB and minimal medium bouillon) the GTs do not change significantly up to the fifth passage. From the sixth passage on, faster growing GVR clones (graded shortening of GT) accumulate in the original vaccine strain populations (GT about 31 to 32; wild strain about 22 minutes). This process takes place in separate steps with different speed. The GTs between the 10th and the 15th passage differ between 29 and 27 minutes, up to the 30th passage GT of ≦25 minutes can occur. With further passages clones with even shorter GTs are likely.

Remark: On solid media the GTs remain unchanged until the 20th passage tested (lower number of divisions (overvaccination with loop)=dilution down to population level or other selective pressure?).

Unchanged or Only Slightly Lower Attenuation Level of *S.typhimurium* GVR Strains in Comparison to the Original Vaccine Strain:

original strain and GVR strains: five mice each (Prob 01: laboratory of the University of Leipzig) receive i. p. $10^5$, $10^6$ and $10^7$ cfu wild strain: five mice each receive i. p. $10^3$ and $10^5$ cfu.

The animals which died within a period of two weeks are determined.

| *S. typhimurium* GVR strains | | passages | GT (min) | No. dead/ 15 mice |
|---|---|---|---|---|
| Nal 2/Rif 9-GVR: Mm A 11/Rtt | | 11 | 28,0 | 3 Wh 3 |
| GVR: Mm C 11/Rtt | | 11 | 28,5 | 1 |
| GVR: Mm E 11/Rtt | | 11 | 27,0 | 7 |
| GVR: Nb A 15/Rtt | | 15 | 29,0 | 4 |
| GVR: Nb B 15/Rtt | | 15 | 28,5 | 7 Wh 4 |
| GVR: Nb B 25/Rtt | | 25 | 27,0 | 2 |
| GVR: Nb C 15/Rtt | | 15 | 28,5 | 0 Wh 0 |
| GVR: Nb D 15/Rtt | | 15 | 28,5 | 2 |
| GVR: Nb D 25/Rtt | | 25 | 28,0 | 1 |
| GVR: Nb E 15/Rtt | | 15 | 28,5 | 2 |
| GVR: LB A 15/Rtt | | 15 | 28,5 | 3 |
| GVR: LB B 15/Rtt | | 15 | 28,5 | 5 |
| GVR: LB C 15/Rtt | | 15 | 28,0 | 7 Wh 4 |
| GVR: LB C 25/Rtt | | 25 | 26,0 | 7 |
| GVR: LB D 15/Rtt | | 15 | 28,5 | 0 Wh 0 |
| GVR: LB D 25/Rtt | | 25 | 26,5 | 0 |
| GVR: LB E 15/Rtt | | 15 | 27,0 | 7 Wh 4 |
| *Ssq/Sm 60/Rif 42-GVR III 12 | | 12 | 29,0 | 7 |
| GVR III 16 | | 16 | 28,0 | 8 |
| GVR I 30 | | 30 | 28,5 | 8 |
| GVR II 30 | | 30 | 26,0 | 9 |
| Nal 2/Rif 9/Rtt | three parallel tests | | 32,0 | 4 Wh 6, 7 |
| prototype | four tests 1992–1990 | | | 5, 8, 5, 6 |
| wild strain control | i.p. $10^3$ cfu = ≧ 14; i.p. $10^5$ cfu = 15 | | | |

Mm: liquid minimum medium
Nb: nutrient bouillon
LB: LB-Bouillon
Wh: animal test repeated with same strain
**S. tm* Ssq/Sm 60/Rif 42 original strain; GT: 31 minutes Apart from a few apparently slightly higher (or slightly lower) attenuated clones, the GVR strains tested show a variation in their attenuation behavior which corresponds to the variation of the original strain values determined in seven separate approaches 1993–1990, and which are within the variation under test conditions. Even if a few GVR strains are attenuated slightly lower, this is irrelevant for the practice: the differences in the $LD_{50}$ mouse in comparison to the wild strain (i. p. $LD_{50}$ mouse about $10^1$ cfu) of about five logarithmic steps are retained.

In the case of strain-dependent separation of GVRs with perhaps significantly lower attenuation level (and possibly not leading to acceptable side effects) preferrably vaccine strains with a higher (up to the border of overattenuation) attenuation are used for the isolation of optimally attenuated suppressor mutants.

In other words: The GVRs are (like Sm-id and T-tol strains, Linde. K.: Arch. exper. Vet. med. 1978, 32, 943–949) no back mutants but apparently intra and intergenetical suppressor mutants still having their attenuation markers and an attenuation level which varies around the original value of the vaccine strain.

For the detection of the unchanged invasive capacity in comparison to the original vaccine strains ≦36 hours old chicks orally received $10^9$ cfu of the GVR. After five and eight days the germ count/gram liver was determined quantitatively (see example 2) as well as qualitatively by means of the accumulation (nutrient media with 100 μg streptomycin and rifampicin/ml in the case of the GVRs of the Ssq/Sm/Rif strains, or 100μg rifampicin and 12.5 μg nalidixic acid/ml in the case of the GVRs of the Nal/Rif/Rtt strain): the germ counts of the GVRs in the chick's liver more or less correspond to the values of the original vaccine strains. With respect to S. infantis and S. anatum lower germ counts are found in the wild strain, the original strain as well as in the selected GVRs in comparison to S. enteritidis and S. typhimurium, which corresponds to U. Methner's observation (doctoral thesis, University of Leipzig, Veterinary Medical Faculty, 1991) that S. infantis is less invasive for chickens.

Therefore, the revertants having a shortened generation time, as e. g. S. tm Ssq/Sm 60/Rif 42/-GVR II 30, S. ent Ssq/Sm 24/Rif 12/-GVR II 30, S. inf Ssq/Sm 153/Rif 7/-GVR II 30, S. ana Ssq/Sm 81/Rif 21/-GVR II 30, are ideal as salmonella vaccine strains having an extreme stability in the attenuation (total stability of the attenuation markers reducing virulence at least ≦$10^{-21}$: Sm×Rif×suppressor mutation) (see also table at the end).

EXAMPLE 2

Macrolide Tolerant Revertants (MTR), Derived from the Ssq (Envelope) Marker of the Sm/Rif Metabolic Drift Attenuated Vaccine Strains for Chicks/chickens, as Salmonella Vaccine Strains Having an Increased Stability in the Antiepidemic Potency.

$10^8$ to $10^9$ cfu of the Ssq/Sm/Rif original strains are transferred onto nutrient agar containing 20 μg erythromycin/ml (or in the two step procedure at first onto 5 to 10 μg erythromycin/ml and from this culture onto 20 μg erythromycin/ml) by means of a spatula, and the grown colonies/clones are tested with respect to the macrolide tolerance they obtained after about ten passages on nutrient agar. The tolerance/sensitivity of these macrolide tolerant revertants to Na-desoxycholate, Na-dodecylsulphate as well as a. o. ciprofloxacin (presently the most effective antibiotic against Salmonella), chloramphenicol and doxycycline generally corresponds to the values of the wild strain, individual revertants of S. enteritidis, however, still have the up to four times higher (super)-sensitivity of the original strain to ciprofloxacin.

The death kinetics ($10^6$ cfu/ml starting germ count) in water at 37 ° C. (as an indirect measure for the environmental resistance) does not show the values of the wild strain, since there is a variation (in comparison to the wild strain/vaccine strain without envelope marker) in the life span of the vaccine strain, which is shortened to about two thirds.

A selection of these revertant—with respect to a similar as or even shorter survival span in water in comparison to the original vaccine strain and, with respect to S. enteritidis, the remaining supersensitivity to ciprofloxacin—was tested in the chick model in comparison to the vaccine strain with respect to invasion and excretion behavior. For this, ≦36 hours old chicks orally received $10^9$ cfu of the respective original vaccine strains and of the macrolide tolerant revertants derived from those:

Detection of invasive capacity: After five and eight days the germ count/gram liver was determined quantitatively (liver homogenate in 5 ml PBS, 3×0.1 ml spread by means of a spatula; border of detection ≦20 germs/gram) as well as qualitatively by means of the accumulation in nutrient bouillon containing an antibiotic additive (see example 1).

Testing the excretion behavior: Over a period of twelve days the salmonella germ counts are determined in the faeces as a thousandth of the coli population, and these values are compared to those of an additional comparative vaccine strain S. tm Nal 2/Rif 9 without envelope marker (with the same i. p. $LD_{50}$ mouse and similar prolongation of generation time as e. g. the S. tm Ssq/Sm 60/Rif 42).

Also in this model, the macrolide tolerant revertants show a similar behavior to that of the original vaccine strain (with envelope marker);

Invasive capacity: The germ counts of the revertants in the chicken liver correspond to the values of the original vaccine strain. With respect to S. infantis and S. anatum lower germ counts are found in the wild strain, the original vaccine strain as well as in the selected revertants in comparison to S. enteritidis and S. typhimurium, which, however, corresponds to U. Methner's observation (doctoral thesis, University of Leipzig, veterinary Medical Faculty, 1991) that S. infantis is less invasive for chickens.

Excretion behaviour: The quantitative excretion behavior of the macrolide tolerant revertants, determined from the thousandth part of enterobacteria, approximately corresponds to that of the original vaccine strains and drops below the 0.1 thousandth border within five to six days.

In other words: The similar or partly even faster death rate in water with respect to the tested macrolide tolerant revertants in comparison to the original vaccine strains as well as the de facto identical excretion behaviour (and the unchanged invasive capacity) in chicks indirectly proves that these strains are no back mutants in the envelope marker and, therefore, the Ssq marker in the original strains has a much higher stability than the reversion frequency of ≦$10^{-8}$ given in the phylogenetic pass.

Therefore, the macrolide tolerant revertants, as e. g. S. tm Ssq-MTR 16/Sm 60/Rif 42, S. ent Ssq-MTR 25/Sm 24/Rif 12, S. inf Ssq-MTR 12/Sm 153/Rif 7 and S. ana Ssq-MTR 23/Sm 81/Rif 21, are ideal as vaccine strains having an increased stability in the antiepidemic potency (total stability=product of the individual stabilities of the Ssq marker and the suppressor mutations) (see following table).

SUPPLEMENT: TABLE WITH RESPECT TO EXAMPLES 1 AND 2

GVR derived from metabolic drift attenuated double marker (original) vaccine strains with envelope marker as well as MTR*: De facto unchanged invasive capacity (germ count/gram liver five and eight days after oral application of $10^9$ cfu to ≦36 hours old chicks); remaining antiepidemic potency of the MTR* (death kinetics of $10^6$ cfu/ml in water at 37° C.)

| Salmonella | strains | | GT (min) | Ø germ count/gram liver fifth day | eight day | cfu water ninth day |
|---|---|---|---|---|---|---|
| *typhimurium* | wild strain | 60/Rif 42 | 22,0 | $6,0 \times 10^3$ | nt | $4 \times 10^5$ |
| | Ssq/Sm | | 31,0 | $1,5 \times 10^3$ | $2,8 \times 10^2$ | $4 \times 10^3$ |
| | GVR | II/30 | 26,0 | $2,5 \times 10^3$ | $6,3 \times 10^2$ | |
| | GVR | III/16 | 28,0 | $1,5 \times 10^3$ | $2,8 \times 10^2$ | |
| | MTR | 16 | | $1,0 \times 10^3$ | $1,4 \times 10^2$ | $1 \times 10^4$ |
| | MTR | 40 | | $1,5 \times 10^3$ | $5,6 \times 10^2$ | $1 \times 10^4$ |
| *enteritidis* | wild strain | 24/Rif 12 | 22,0 | $5,0 \times 10^3$ | nt | $3 \times 10^5$ |
| | Ssq/Sm | | 32,0 | $4,0 \times 10^3$ | nt | $2 \times 10^4$ |
| | GVR | II/30 | 28,0 | $4,5 \times 10^3$ | $5,3 \times 10^2$ | |
| | GVR | IV/16 | 27,0 | $2,0 \times 10^3$ | nt | |
| | MTR | 2 | | $2,5 \times 10^3$ | $1,9 \times 10^2$ | $5 \times 10^3$ |
| | MTR | 25 | | $2,5 \times 10^3$ | $5,6 \times 10^2$ | $7 \times 10^3$ |
| *anatum* | wild strain | 81/Rif 21 | 22,0 | $1,5 \times 10^2$ | nt | $4 \times 10^4$ |
| | Ssq/Sm | | 32,0 | $3,5 \times 10^1$ | accumulation | $1 \times 10^4$ |
| | GVR | II/30 | 26,5 | $1,0 \times 10^2$ | mostly | |
| | GVR | III/16 | 27,5 | $2,0 \times 10^2$ | positive | |
| | MTR | 5 | | $3,5 \times 10^1$ | | $1 \times 10^4$ |
| | MTR | 23 | | $7,0 \times 10^1$ | | $1 \times 10^4$ |
| *infantis* | wild strain | 153/Rif 7 | 22,0 | $2,0 \times 10^2$ | nt | $5 \times 10^5$ |
| | Ssq/Sm | | 31,0 | $1,0 \times 10^2$ | accumulation | $6 \times 10^4$ |
| | GVR | II/30 | 25,0 | $7,0 \times 10^1$ | mostly | |
| | GVR | III/24 | 28,5 | $1,0 \times 10^2$ | positive | |
| | MTR | 12 | | $2,0 \times 10^2$ | | $7 \times 10^4$ |
| | MTR | 28 | | $2,0 \times 10^2$ | | $6 \times 10^4$ |

*MTR: Doctoral theses of Adler, T. and Jaensch, C. (1993/94)

I claim:

1. A live Salmonella vaccine comprising one or more suppressor mutant Salmonella strains that are derived from original live metabolic drift attenuated vaccine strains, said mutant Salmonella strains having an increased stability in at least one attenuating metabolic drift marker and an attenuation level adapted to the sensitivity of a host species, wherein each mutant Salmonella strain has a shortened generation time which has been shortened from about 31–32 minutes to ≦27 minutes and/or an increased macrolide tolerance whereby the minimum inhibitory concentration (MIC) toward erythromycin increases from ≦5 ug/mL to ≧20 ug/mL, in comparison to the original live vaccine strains from which said mutant Salmonella strains were derived.

2. A method for immunization of a host against Salmonella diseases by administration of the live Salmonella vaccine according to claim 1.

3. A method for immunization of chicks and chickens against Salmonella diseases comprising oral or parenteral administration of the live Salmonella vaccine according to claim 1.

* * * * *